(12) United States Patent
Gazeau

(10) Patent No.: US 6,695,236 B2
(45) Date of Patent: Feb. 24, 2004

(54) PROCESS AND DEVICE FOR THE EXTRACTION OF DNA, RNA AND PROTEINS FROM BIOLOGICAL SAMPLES

(75) Inventor: Michel Gazeau, Collonges sous Saleve (FR)

(73) Assignee: Genomic, S.A. (FR)

( * ) Notice: Subject to any disclaimer, the term of this patent is extended or adjusted under 35 U.S.C. 154(b) by 0 days.

(21) Appl. No.: 10/007,043

(22) Filed: Nov. 5, 2001

(65) Prior Publication Data

US 2002/0066812 A1 Jun. 6, 2002

Related U.S. Application Data

(63) Continuation of application No. PCT/FR00/01230, filed on May 5, 2001.

(30) Foreign Application Priority Data

May 5, 1999 (FR) .............................................. 99 05795
Aug. 2, 1999 (FR) .............................................. 99 10040

(51) Int. Cl.$^7$ ................................................ B02C 19/12
(52) U.S. Cl. ............................................. 241/2; 241/23
(58) Field of Search ........................... 241/1, 2, 23, 66, 241/189.1

(56) References Cited

FOREIGN PATENT DOCUMENTS

| EP | 0 123 316 A2 | 10/1984 |
|---|---|---|
| EP | 0 487 028 A2 | 5/1992 |
| WO | WO 96/15576 | 5/1996 |
| WO | WO 98/20164 | 5/1998 |

*Primary Examiner*—Mark Rosenbaum
(74) *Attorney, Agent, or Firm*—Piper Rudnick LLP

(57) ABSTRACT

A device for grinding biological samples to extract DNA, RNA and proteins including a multiplicity of rotary hammers supported by a hammer-carrier block and a lower mobile tray, the tray being movable between an operating position close to the hammer-carrier block and a rest position away from the hammer-carrier block, each of the hammers comprising at least one conduit for distribution of liquid.

12 Claims, 3 Drawing Sheets

PROCESS AND DEVICE FOR THE EXTRACTION OF DNA, RNA AND PROTEINS FROM BIOLOGICAL SAMPLES

RELATED APPLICATION

This is a continuation of International Application No. PCT/FR00/01230, with an international filing date of May 5, 2001, which is based on French Patent Application Nos. 99/05795, filed May 5, 1999, and 99/10040, filed Aug. 2, 1999.

FIELD OF THE INVENTION

This invention pertains to the field of the high-yield extraction of DNA, RNA and proteins from nonliquid biological samples or cells in suspension, in the natural state or in preparations, e.g., alimentary preparations.

BACKGROUND

Known in the state of the art are various processes for extracting nucleic acids and proteins from samples that employ an initial step of grinding the sample by means of various processes such as crushing, ultrasound, high pressure, etc.

It is valuable with soft samples to grind them at very low temperature to diminish the risks of degradation of the macromolecules and facilitate the breaking up of the cells and, thus, improve the yield of the extractions. This is followed by various treatments of the sample designed to wash it, eliminate the cell membranes and undesired products. The first step is not systematically implemented.

SUMMARY OF THE INVENTION

This invention relates to a device for grinding biological samples to extract DNA, RNA and proteins including a multiplicity of rotary hammers supported by a hammer-carrier block and a lower mobile tray, the tray being movable between an operating position close to the hammer-carrier block and a rest position away from the hammer-carrier block, each of the hammers including at least one conduit for distribution of liquid.

Figure 1:
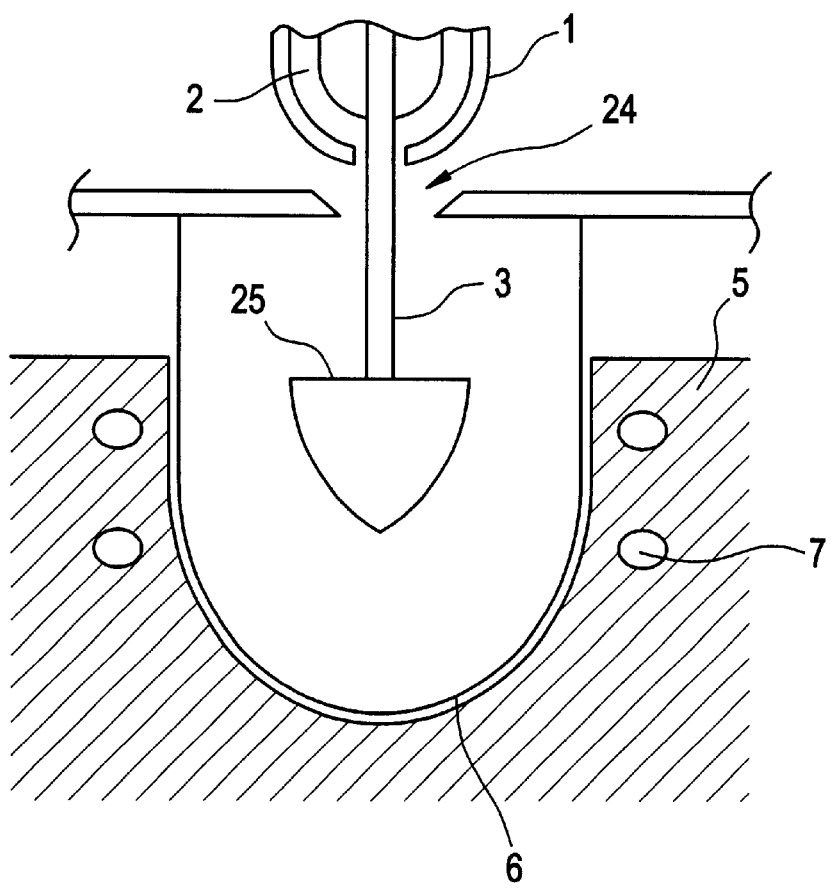
FIG. 1 shows a partial enlarged view of a device according to the invention.

Better understanding of the invention will be obtained upon reading the description below which makes reference to a nonlimitative example of implementation and to the attached figures. The process in accordance with the invention is comprised of the following steps:

after grinding a low temperature (temperature lower than room temperature by various processes substantially simultaneously a number of samples, adding automatically and with a minimal delay a sufficiently precise volume of liquid.

One of the liquids can be preferably a lysis buffer of the cell walls or, more precisely, a denaturing lysis buffer.

As a consequence, the invention prevents the action of agents that can degrade the macromolecules while allowing the flow of the liquid(s) even if the grinding took place at very low temperature (below 0° C.).

The invention limits the risks of contamination of persons, e.g., by viruses, and diminishes the loss of biological material that adheres to the grinding equipment. The invention allows treatment of multiple samples simultaneously and linking operations and their automation.

The invention also pertains to a device for grinding biological samples for the purpose of extracting DNA, RNA and proteins, comprising a multiplicity of rotary hammers supported by a hammer-carrier block and a lower mobile tray, which can move between an operating position close to the hammer-carrier block and a rest position away from the hammer-carrier block, with each of the hammers comprising at least one conduit for the distribution of liquid. The lower tray advantageously presents means for receiving tubes laid out in an arrangement conforming to that of the hammers or a multiplicity of cups laid out in an arrangement conforming to that of the hammers. According to a variant, the device furthermore comprises means to enable the flow of the liquid(s) by gravity upon the opening of solenoid valves.

The preferred device, described as an example, is constituted of the following elements:

The base grinding equipment which is intended for plant-based samples for which only the proteins are of importance, to which is added:

A device constituted of a network of nozzles each positioned close to the shaft of each hammer, communicating via catheters with the reservoir(s) of the liquid(s) to be distributed. The reservoirs can be maintained at defined temperatures. The liquid(s) can flow via gravity upon opening of solenoid valves and the volume distributed can be regulated on the basis of the precise length and diameter of the catheters by adjusting the duration of opening of the solenoid valves. Another solution is, e.g., to aspirate and force the flow of the liquid(s) by means of precision pumps. In this case, it is easy to purge the catheters. The shafts of the hammer can operate as guides for the flow of the liquid(s) to the samples. In all cases, the distribution of the liquid is performed on one or more subsets of tubes. If a subset of 24 tubes is selected from the total set of 96 tubes, or if only a portion of the grinding positions is occupied, it is possible to treat only 24 samples of larger volume and avoid wasting the liquid.

Regulated heating devices which can be resistors embedded in the tube-carrier tray of the grinding equipment and/or infrared heating elements positioned around the operating space.

If desired, a rigid plate, traversed by the shafts of the hammers can be added to the preferred device for covering each of the samples in its container during grinding so as to prevent cross contamination. Because of the milling for passage of the hammer shafts on its top part, this plate promotes the uniform flow of the liquid(s) into each container of sample, around the hammers and contributes to the removal of adherent fragments.

The programmable automation system that controls the grinding equipment also controls the flows of liquid, the temperature and the closing of the rigid plate.

The device is constituted by an automated system formed by a frame comprising two mobile blocks. The upper block is a tray supporting a multiplicity of rotary hammer carriers (1) arranged, e.g., to form a matrix of 96 heads. The hammers are inter-changeable and can exhibit a variety of sizes or shapes. The rotation rate of the hammers is between about 100 and about 1100 revolutions per minute. A control program can determine the duration, rate and direction of rotation, the pressure and the various desired parameters of the grinding process. The equipment includes a memory for recording multiple grinding profiles.

The automated system performs the following functions:

holding the hammers, washing and decontamination of the hammers, bringing the hammers to the selected temperature, grinding soft samples, grinding grains, special grindings, extraction of the hammers.

The system also has a detector that inactivates the device when the operator accesses the operating space enclosed by the upper and lower trays.

Turning now to the drawings, the lower block (5) is a mobile tray which supports interchangeable racks exhibiting means for receiving tubes filled with the samples to be ground or cups to directly receive biological materials such as grains.

The tubes are held in transparent 6-tube supports. Four 6-tube supports occupy the surface of one microplate, which makes it possible to centrifuge 96 tubes at a time on a suitable rotor. In the case of grinding grains, the tray is in the form of a set of high-carbon stainless steel cups the bottoms of which can be open or closed, and the hammers have multiple facets. The product of the grinding is then recovered in tubes placed under the cups.

The lower block is vertically mobile to allow penetration of the hammers (24) into the tubes (6) or cups, and to move the hammers (24) away for loading or unloading the equipment. The lower tray (5) is thermostated, e.g., by conduits for the circulation of a coolant. An additional cover plate can be provided on the tube-carrier tray.

The various blocks are removable and can be removed from the device by a simple sliding forward. The hammer carrier (1) has a liquid inflow conduit. The liquid flows down the shaft (3) of the hammer (24) to the head of the hammer (25). The hammers (24) can be washed and dried automatically by injection of liquids via the conduits (2) or by rotating them at high velocities. When the hammers (24) move out of the tubes (6), they are completely immobile because it is the tube carrier tray that moves or descends away. This mode of operating prevents the dissemination of biological material used as substrate for PCR analysis.

Figure 2:
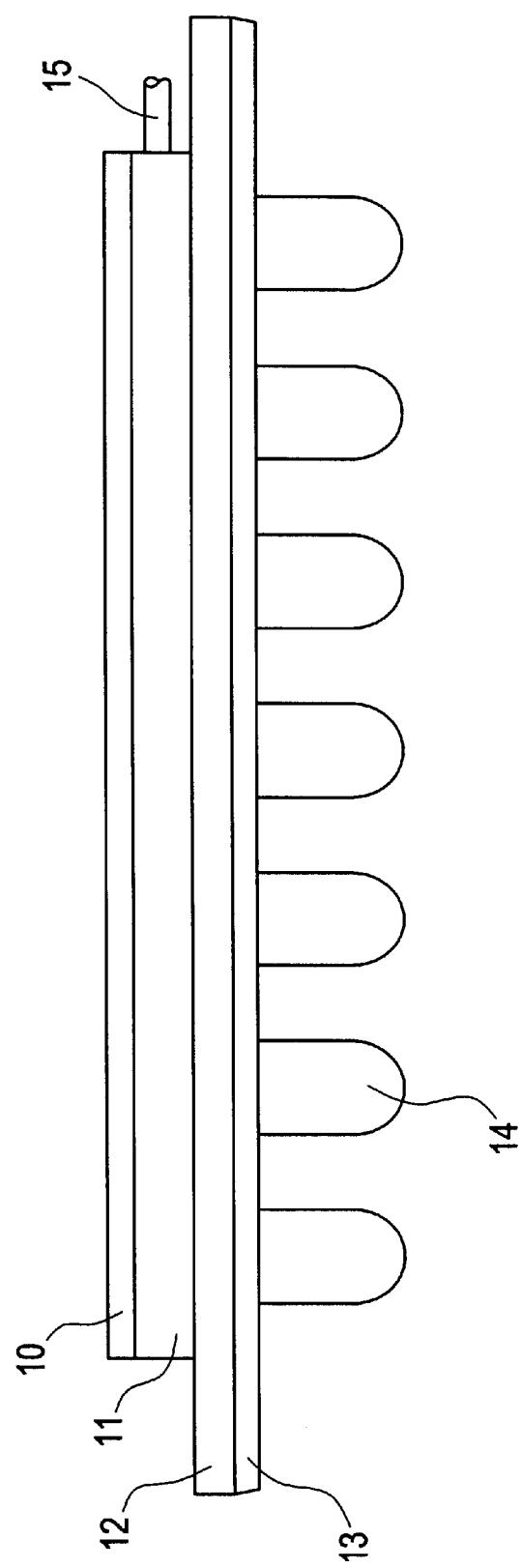
FIG. 2 shows a sectional view of a variant of implementation.
Figure 3:
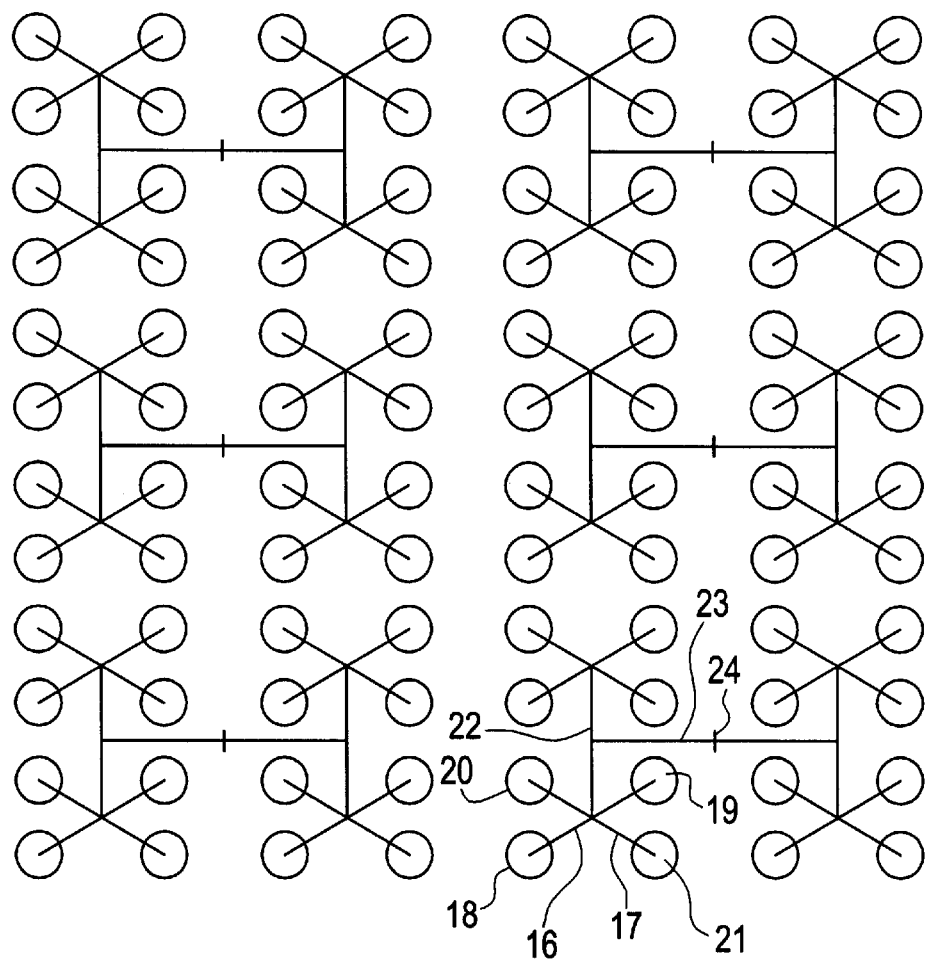
FIG. 3 shows a schematic view of the cover for the device shown in FIG. 2.

FIG. 2 shows a sectional view of a variant of implementation and FIG. 3 shows a schematic view of the cover plate for said device.

The cover plate is composed of a superposition of plates (10 to 13). It covers the tubes (14) for feeding the tubes with reactants and buffers.

It comprises an upper plate (10) made of steel or aluminum, and two intercalary plates (11, 12) made of Teflon as well as a lower plate (13) made of silicone such that the tubes are sealed tightly (14). The lower plate (13) made of silicone is pierced by holes corresponding to the openings of the tubes.

The intercalary plates (11, 12) have milled channels as shown in FIG. 3. These channels form a network for the distribution of the fluids originating from a feed conduit (15) shown in FIG. 2 to the openings of each of the tubes. These channels form in the plate (12) series of cross passages constituted of two arms (16, 17) each connecting two openings respectively (18, 19), (20, 21). These cross passages are connected in pairs by connecting arms (22) which join the intersection of the arms of two adjacent cross passages. Two connecting arms (22) are in turn connected by collector arms (23), connecting the middle of the two connecting arms. These collector arms (23) empty into a feeding network formed by grooves in the plate (11), which finally empty into the feeding conduit (15).

The arms are determined in a manner such that their trajectories reaching the various tubes are substantially identical. The connections between the different arms are symmetrical.

What is claimed is:

1. A device for grinding biological samples to extract DNA, RNA and proteins comprising:

a multiplicity of rotary hammers supported by a hammer-carrier block and a lower mobile tray, the tray being movable between an operating position close to the hammer-carrier block and a rest position away from the hammer-carrier block, each of the hammers having a hammer-carrier comprising at least one conduit for distribution of liquid.

2. The device according to claim 1, wherein the lower tray includes means for receiving tubes positioned in an arrangement conforming to that of the hammers.

3. The device according to claim 1, wherein the lower tray includes a multiplicity of cups laid out in an arrangement conforming to that of the hammers.

4. The device according to claim 3, wherein the lower tray comprises regulated heating devices.

5. The device according to claim 1, further comprising means connected to enable flow of liquid by gravity upon opening of solenoid valves.

6. The device according to claim 1, further comprising pumps and means for purging catheters connected to reservoirs of liquid to be distributed.

7. The device according to claim 1, further comprising a rigid plate traversed by the shafts of the hammers for covering each of the samples in its container during grinding to prevent cross contamination.

8. The device according to claim 1, further comprising a cover plate composed of a superposition of plates, with intercalary plates including a milled network leading to orifices for feeding tubes.

9. The device according to claim 8, wherein the cover comprises an upper plate and two intercalary plates made of tetrafluoroethylene as well as a lower plate made of silicone to assure that the tubes are sealed tightly.

10. The device according to claim 9, wherein milled network includes channels forming a network for distribution of fluids originating from a feed conduit to openings of each of the tubes.

11. The device according to claim 10, wherein the channels form in the plate a series of cross passages constituted of two arms, each connecting two openings respectively, with the cross passages being connected in pairs by connecting arms which join an intersection of the arms of two adjacent cross passages, two connecting arms being in turn connected by collector arms, connecting the middle of the two connecting arms.

12. The device according to claim 1, further comprising a network of nozzles, each positioned close to the shaft of each hammer and communicating via catheters with one or more reservoirs of the liquid to be distributed.

* * * * *